(12) United States Patent
Johnson et al.

(10) Patent No.: US 6,627,733 B2
(45) Date of Patent: Sep. 30, 2003

(54) RECEPTOR TYROSINE KINASE WITH A DISCOIDIN-TYPE BINDING DOMAIN

(76) Inventors: Jeffrey D. Johnson, 1454-27th Ave., San Francisco, CA (US) 94122; William J. Rutter, 80 Everson, San Francisco, CA (US) 94131; Jeffrey C. Edman, 126 Marion Ave., Mill Valley, CA (US) 94941

( * ) Notice: Subject to any disclaimer, the term of this patent is extended or adjusted under 35 U.S.C. 154(b) by 0 days.

(21) Appl. No.: 09/140,378

(22) Filed: Aug. 26, 1998

(65) Prior Publication Data

US 2003/0124133 A1 Jul. 3, 2003

Related U.S. Application Data

(63) Continuation-in-part of application No. 08/292,299, filed on Aug. 16, 1994, now abandoned, which is a continuation-in-part of application No. 08/077,254, filed on Jun. 14, 1993, now abandoned.

(51) Int. Cl.[7] .................................................. C07K 1/00
(52) U.S. Cl. ...................... 530/350; 435/69.1; 435/194; 436/501; 514/2; 536/23.5
(58) Field of Search ........................... 530/350; 435/194, 435/69.1; 514/2; 536/23.5; 436/501

(56) References Cited

U.S. PATENT DOCUMENTS 5,677,144 A * 10/1997 Ullrich ...................... 435/69.1
6,051,397 A     4/2000 Ullrich et al.

* cited by examiner

Primary Examiner—Yvonne Eyler
Assistant Examiner—Michael Brannock
(74) Attorney, Agent, or Firm—Townsend and Townsend and Crew LLP

(57) ABSTRACT

A breast carcinoma tyrosine phosphoprotein, DDR (Discoidin Domain Receptor), that defines a novel class of receptor tyrosine kinases is presented. The DDR cDNA predicts a polypeptide C-terminal tyrosine kinase domain and an N-terminal domain similar to the *Dictyostelium discoideum* lectin discoidin I. These domains are connected by an extraordinary hydrophilic proline/glycine-rich domain, which is interrupted by a predicted transmembrane sequence. This extended proline/glycine-rich region suggests an unusual geometry of interaction with ligand or substrates. Discoidin I-type domains may interact with specific cell surface molecules.

2 Claims, 12 Drawing Sheets

Figure 1a

CCCGGGTCGG ACCGCCTGGG TCTGCCGGGA AGAGCGATGA

GAGGTGTCTG AAGGTGGCTA TTCACTGAGC GATGGGGTTG

GACTTGAAGG AATGCCAAGA GATGCTGCCC CCACCCCCTT

AGGCCCGAGG GATCAGGAGC T

| | | | | | | | | | ATG<br>Met<br>1 | GGA<br>Gly | CCA<br>Pro |
|---|---|---|---|---|---|---|---|---|---|---|---|
| GAG<br>Glu | GCC<br>Ala<br>5 | CTG<br>Leu | TCA<br>Ser | TCT<br>Ser | TTA<br>Leu | CTG<br>Leu<br>10 | CTG<br>Leu | CTG<br>Leu | CTC<br>Leu | TTG<br>Leu | GTG<br>Val<br>15 |
| GCA<br>Ala | AGT<br>Ser | GGA<br>Gly | GAT<br>Asp | GCT<br>Ala<br>20 | GAC<br>Asp | ATG<br>Met | AAG<br>Lys | GGA<br>Gly | CAT<br>His<br>25 | TTT<br>Phe | GAT<br>Asp |
| CCT<br>Pro | GCC<br>Ala | AAG<br>Lys<br>30 | TGC<br>Cys* | CGC<br>Arg | TAT<br>Tyr | GCC<br>Ala | CTG<br>Leu<br>35 | GGC<br>Gly | ATG<br>Met | CAG<br>Gln | GAC<br>Asp |
| CGG<br>Arg<br>40 | ACC<br>Thr | ATC<br>Ile | CCA<br>Pro | GAC<br>Asp | AGT<br>Ser<br>45 | GAC<br>Asp | ATC<br>Ile | TCT<br>Ser | GCT<br>Ala | TCC<br>Ser<br>50 | AGC<br>Ser |
| TCC<br>Ser | TGG<br>Trp | TCA<br>Ser | GAT<br>Asp<br>55 | TCC<br>Ser | ACT<br>Thr | GCC<br>Ala | GCC<br>Ala | CGC<br>Arg<br>60 | CAC<br>His | AGC<br>Ser | AGG<br>Arg |
| TTG<br>Leu | GAG<br>Glu<br>65 | AGC<br>Ser | AGT<br>Ser | GAC<br>Asp | GGG<br>Gly | GAT<br>Asp<br>70 | GGG<br>Gly | GCC<br>Ala | TGG<br>Trp | TGC<br>Cys* | CCC<br>Pro<br>75 |
| GCA<br>Ala | GGG<br>Gly | TCG<br>Ser | GTG<br>Val | TTT<br>Phe<br>80 | CCC<br>Pro | AAG<br>Lys | GAG<br>Glu | GAG<br>Glu | GAG<br>Glu<br>85 | TAC<br>Tyr | TTG<br>Leu |
| CAG<br>Gln | GTG<br>Val | GAT<br>Asp<br>90 | CTA<br>Leu | CAA<br>Gln | CGA<br>Arg | CTC<br>Leu | CAC<br>His<br>95 | CTG<br>Leu | GTG<br>Val | GCT<br>Ala | CTG<br>Leu |
| GTG<br>Val<br>100 | GGC<br>Gly | ACC<br>Thr | CAG<br>Gln | GGA<br>Gly | CGG<br>Arg<br>105 | CAT<br>His | GCC<br>Ala | GGG<br>Gly | GGC<br>Gly | CTG<br>Leu<br>110 | GGC<br>Gly |
| AAG<br>Lys | GAG<br>Glu | TTC<br>Phe | TCC<br>Ser | CGG<br>Arg<br>115 | AGC<br>Ser | TAC<br>Tyr | CGG<br>Arg | CTG<br>Leu | CGT<br>Arg<br>120 | TAC<br>Tyr | TCC<br>Ser |

Figure 1b

| CGG | GAT | GGT | CGC | CGC | TGG | ATG | GGC | TGG | AAG | GAC | CGC |
|---|---|---|---|---|---|---|---|---|---|---|---|
| Arg | Asp | Gly | Arg | Arg | Trp | Met | Gly | Trp | Lys | Asp | Arg |
|  | 125 |  |  |  |  | 130 |  |  |  |  | 135 |

| TGG | GGT | CAG | GAG | GTG | ATC | TCA | GGC | AAT | GAG | GAC | CCT |
|---|---|---|---|---|---|---|---|---|---|---|---|
| Trp | Gly | Gln | Glu | Val | Ile | Ser | Gly | Asn | Glu | Asp | Pro |
|  |  |  |  | 140 |  |  |  |  | 145 |  |  |

| GAG | GGA | GTG | GTG | CTG | AAG | GAC | CTT | GGG | CCC | CCC | ATG |
|---|---|---|---|---|---|---|---|---|---|---|---|
| Glu | Gly | Val | Val | Leu | Lys | Asp | Leu | Gly | Pro | Pro | Met |
|  |  | 150 |  |  |  |  | 155 |  |  |  |  |

| GTT | GCC | CGA | CTG | GTT | CGC | TTC | TAC | CCC | CGG | GCT | GAC |
|---|---|---|---|---|---|---|---|---|---|---|---|
| Val | Ala | Arg | Leu | Val | Arg | Phe | Tyr | Pro | Arg | Ala | Asp |
| 160 |  |  |  |  | 165 |  |  |  |  | 170 |  |

| CGG | GTC | ATG | AGC | GTC | TGT | CTG | CGG | GTA | GAG | CTC | TAT |
|---|---|---|---|---|---|---|---|---|---|---|---|
| Arg | Val | Met | Ser | Val | Cys | Leu | Arg | Val | Glu | Leu | Tyr |
|  |  |  | 175 |  | * |  |  |  | 180 |  |  |

| GGC | TGC | CTC | TGG | AGG | GAT | GGA | CTC | CTG | TCT | TAC | ACC |
|---|---|---|---|---|---|---|---|---|---|---|---|
| Gly | Cys | Leu | Trp | Arg | Asp | Gly | Leu | Leu | Ser | Tyr | Thr |
|  | *185 |  |  |  |  | 190 |  |  |  |  | 195 |

| GCC | CCT | GTG | GGG | CAG | ACA | ATG | TAT | TTA | TCT | GAG | GCC |
|---|---|---|---|---|---|---|---|---|---|---|---|
| Ala | Pro | Val | Gly | Gln | Thr | Met | Tyr | Leu | Ser | Glu | Ala |
|  |  |  |  | 200 |  |  |  |  | 205 |  |  |

| GTG | TAC | CTC | AAC | GAC | TCC | ACC | TAT | GAC | GGA | CAT | ACC |
|---|---|---|---|---|---|---|---|---|---|---|---|
| Val | Tyr | Leu | Asn | Asp | Ser | Thr | Tyr | Asp | Gly | His | Thr |
|  |  | 210 |  |  |  |  | 215 |  |  |  |  |

| GTG | GGC | GGA | CTG | CAG | TAT | GGG | GGT | CTG | GGC | CAG | CTG |
|---|---|---|---|---|---|---|---|---|---|---|---|
| Val | Gly | Gly | Leu | Gln | Tyr | Gly | Gly | Leu | Gly | Gln | Leu |
| 220 |  |  |  |  | 225 |  |  |  |  | 230 |  |

| GCA | GAT | GGT | GTG | GTG | GGG | CTG | GAT | GAC | TTT | AGG | AAG |
|---|---|---|---|---|---|---|---|---|---|---|---|
| Ala | Asp | Gly | Val | Val | Gly | Leu | Asp | Asp | Phe | Arg | Lys |
|  |  |  | 235 |  |  |  |  | 240 |  |  |  |

| AGT | CAG | GAG | CTG | CGG | GTC | TGG | CCA | GGC | TAT | GAC | TAT |
|---|---|---|---|---|---|---|---|---|---|---|---|
| Ser | Gln | Glu | Leu | Arg | Val | Trp | Pro | Gly | Tyr | Asp | Tyr |
|  | 245 |  |  |  |  | 250 |  |  |  |  | 255 |

Figure 1c

| | | | | | | | | | | | |
|---|---|---|---|---|---|---|---|---|---|---|---|
| GTG Val | GGA Gly | TGG Trp | AGC Ser | AAC Asn 260 | CAC His | AGC Ser | TTC Phe | TCC Ser | AGT Ser 265 | GGC Gly | TAT Tyr |
| GTG Val | GAG Glu | ATG Met 270 | GAG Glu | TTT Phe | GAG Glu | TTT Phe | GAC Asp 275 | CGG Arg | CTG Leu | AGG Arg | GCC Ala |
| TTC Phe 280 | CAG Gln | GCT Ala | ATG Met | CAG Gln | GTC Val 285 | CAC His | TGT Cys * | AAC Asn | AAC Asn | ATG Met 290 | CAC His |
| ACG Thr | CTG Leu | GGA Gly | GCC Ala 295 | CGT Arg | CTG Leu | CCT Pro | GGC Gly | GGG Gly 300 | GTG Val | GAA Glu | TGT Cys * |
| CGC Arg | TTC Phe 305 | CGG Arg | CGT Arg | GGC Gly | CCT Pro | GCC Ala 310 | ATG Met | GCC Ala | TGG Trp | GAG Glu | GGG Gly 315 |
| GAG Glu | CCC Pro | ATG Met | CGC Arg | CAC His 320 | AAC Asn | CTA Leu | GGG Gly | GGC Gly | AAC Asn 325 | CTG Leu | GGG Gly |
| GAC Asp | CCC Pro | AGA Arg 330 | GCC Ala | CGG Arg | GCT Ala | GTC Val | TCA Ser 335 | GTG Val | CCC Pro | CTT Leu | GGC Gly |
| GGC Gly 340 | CGT Arg | GTG Val | GCT Ala | CGC Arg | TTT Phe 345 | CTG Leu | CAG Gln | TGC Cys * | CGC Arg | TTC Phe 350 | CTC Leu |
| TTT Phe | GCG Ala | GGG Gly | CCC Pro 355 | TGG Trp | TTA Leu | CTC Leu | TTC Phe | AGC Ser 360 | GAA Glu | ATC Ile | TCC Ser |
| TTC Phe | ATC Ile 365 | TCT Ser | GAT Asp | GTG Val | GTG Val | AAC Asn 370 | AAT Asn | TCC Ser | TCT Ser | CCG Pro | GCA Ala 375 |
| CTG Leu | GGA Gly | GGC Gly | ACC Thr | TTC Phe 380 | CCG Pro | CCA Pro | GCC Ala | CCC Pro | TGG Trp | TGG Trp 385 | CCG Pro |

Figure 1d

| CCT | GGC | CCA | CCT | CCC | ACC | AAC | TTC | AGC | AGC | TTG | GAG |
|---|---|---|---|---|---|---|---|---|---|---|---|
| Pro | Gly | Pro | Pro | Pro | Thr | Asn | Phe | Ser | Ser | Leu | Glu |
| | | 390 | | | | | 395 | | | | |

| CTG | GAG | CCC | AGA | GGC | CAG | CCA | AGG | CCC | GTG | GCC | AAG |
|---|---|---|---|---|---|---|---|---|---|---|---|
| Leu | Glu | Pro | Arg | Gly | Gln | Pro | Arg | Pro | Val | Ala | Lys |
| 400 | | | | | 405 | | | | | 410 | |

| GCC | GAG | GGG | AGC | CCG | ACC | GCC | ATC | CTC | ATC | GGC | TGC |
|---|---|---|---|---|---|---|---|---|---|---|---|
| Ala | Glu | Gly | Ser | Pro | Thr | Ala | Ile | Leu | Ile | Gly | Cys |
| | | | 415 | | | | | 420 | | | |

| CTG | GTG | GCC | ATC | ATC | CTG | CTC | CTG | CTG | CTC | ATC | ATT |
|---|---|---|---|---|---|---|---|---|---|---|---|
| Leu | Val | Ala | Ile | Ile | Leu | Leu | Leu | Leu | Leu | Ile | Ile |
| | 425 | | | | | 430 | | | | | 435 |

| GCC | CTC | ATG | CTC | TGG | CGG | CTG | CAC | TGG | CGC | AGG | CTC |
|---|---|---|---|---|---|---|---|---|---|---|---|
| Ala | Leu | Met | Leu | Trp | Arg | Leu | His | Trp | Arg | Arg | Leu |
| | | | | 440 | | | | | 445 | | |

| CTC | AGC | AAG | GCT | GAA | CGG | AGG | GTG | TTG | GAA | GAG | GAG |
|---|---|---|---|---|---|---|---|---|---|---|---|
| Leu | Ser | Lys | Ala | Glu | Arg | Arg | Val | Leu | Glu | Glu | Glu |
| | | 450 | | | | | 455 | | | | |

| CTG | ACG | GTT | CAC | CTC | TCT | GTC | CCT | GGG | GAC | ACT | ATC |
|---|---|---|---|---|---|---|---|---|---|---|---|
| Leu | Thr | Val | His | Leu | Ser | Val | Pro | Gly | Asp | Thr | Ile |
| 460 | | | | | 465 | | | | | 470 | |

| CTC | ATC | AAC | AAC | CGC | CCA | GGT | CCT | AGA | GAG | CCA | CCC |
|---|---|---|---|---|---|---|---|---|---|---|---|
| Leu | Ile | Asn | Asn | Arg | Pro | Gly | Pro | Arg | Glu | Pro | Pro |
| | | | 475 | | | | | | 480 | | |

| CCG | TAC | CAG | GAG | CCC | CGG | CCT | CGT | GGG | AAT | CCG | CCC |
|---|---|---|---|---|---|---|---|---|---|---|---|
| Pro | Tyr | Gln | Glu | Pro | Arg | Pro | Arg | Gly | Asn | Pro | Pro |
| | 485 | | | | | 490 | | | | | 495 |

| CAC | TCC | GCT | CCC | TGT | GTC | CCC | AAT | GGC | TCT | GCG | TTG |
|---|---|---|---|---|---|---|---|---|---|---|---|
| His | Ser | Ala | Pro | Cys | Val | Pro | Asn | Gly | Ser | Ala | Leu |
| | | | | 500 | | | | | 505 | | |

| CTG | CTC | TCC | AAT | CCA | GCC | TAC | CGC | CTC | CTT | CTG | GCC |
|---|---|---|---|---|---|---|---|---|---|---|---|
| Leu | Leu | Ser | Asn | Pro | Ala | Tyr | Arg | Leu | Leu | Leu | Ala |
| | | 510 | | | | ** | 515 | | | | |

Figure 1e

| ACT | TAC | GCC | CGT | CCC | CCT | CGA | GGC | CCG | GGC | CCC | CCC |
|---|---|---|---|---|---|---|---|---|---|---|---|
| Thr | Tyr | Ala | Arg | Pro | Pro | Arg | Gly | Pro | Gly | Pro | Pro |
|  | 520 |  |  |  | 525 |  |  |  |  |  | 530 |

| ACA | CCC | GCC | TGG | GCC | AAA | CCC | ACC | AAC | ACC | CAG | GCC |
|---|---|---|---|---|---|---|---|---|---|---|---|
| Thr | Pro | Ala | Trp | Ala | Lys | Pro | Thr | Asn | Thr | Gln | Ala |
|  |  |  |  | 535 |  |  |  |  | 540 |  |  |

| TAC | AGT | GGG | GAC | TAT | ATG | GAG | CCT | GAG | AAG | CCA | GGC |
|---|---|---|---|---|---|---|---|---|---|---|---|
| Tyr | Ser | Gly | Asp | Tyr | Met | Glu | Pro | Glu | Lys | Pro | Gly |
|  |  | 545 |  |  |  |  | 550 |  |  |  |  |

| GCC | CCG | CTT | CTG | CCC | CCA | CCT | CCC | CAG | AAC | AGC | GTC |
|---|---|---|---|---|---|---|---|---|---|---|---|
| Ala | Pro | Leu | Leu | Pro | Pro | Pro | Pro | Gln | Asn | Ser | Val |
| 555 |  |  |  |  | 560 |  |  |  |  | 565 |  |

| CCC | CAT | TAT | GCC | GAG | GCT | GAC | ATT | GTT | ACC | CTG | CAG |
|---|---|---|---|---|---|---|---|---|---|---|---|
| Pro | His | Tyr | Ala | Glu | Ala | Asp | Ile | Val | Thr | Leu | Gln |
|  |  |  | 570 |  |  |  |  | 575 |  |  |  |

| GGC | GTC | ACC | GGG | GGC | AAC | ACC | TAT | GCT | GTG | CCT | GCA |
|---|---|---|---|---|---|---|---|---|---|---|---|
| Gly | Val | Thr | Gly | Gly | Asn | Thr | Tyr | Ala | Val | Pro | Ala |
|  | 580 |  |  |  |  | 585 |  |  |  |  | 590 |

| CCT | CCC | CCA | GGG | GCA | GTC | GGG | GAT | GGG | CCC | CCC | AGA |
|---|---|---|---|---|---|---|---|---|---|---|---|
| Pro | Pro | Pro | Gly | Ala | Val | Gly | Asp | Gly | Pro | Pro | Arg |
|  |  |  |  | 595 |  |  |  |  |  | 600 |  |

| GTG | GAT | TTC | CCT | CGA | TCT | CGA | CTC | CGC | TTC | AAG | GAG |
|---|---|---|---|---|---|---|---|---|---|---|---|
| Val | Asp | Phe | Pro | Arg | Ser | Arg | Leu | Arg | Phe | Lys | Glu |
|  |  | 605 |  |  |  |  | 610 |  |  |  |  |

| AAG | CTT | GGC | GAG | GGC | CAG | TTT | GGG | GAG | GTG | CAC | CTG |
|---|---|---|---|---|---|---|---|---|---|---|---|
| Lys | Leu | Gly | Glu | Gly | Gln | Phe | Gly | Glu | Val | His | Leu |
| 615 |  |  |  |  | 620 |  |  |  |  | 625 |  |

| TGT | GAG | GTC | GAC | AGC | CCT | CAA | GAT | CTG | GTT | AGT | CTT |
|---|---|---|---|---|---|---|---|---|---|---|---|
| Cys | Glu | Val | Asp | Ser | Pro | Gln | Asp | Leu | Val | Ser | Leu |
|  |  |  | 630 |  |  |  |  | 635 |  |  |  |

| GAT | TTC | CCC | CTT | AAT | GTG | CGT | AAG | GGA | CAC | CCT | TTG |
|---|---|---|---|---|---|---|---|---|---|---|---|
| Asp | Phe | Pro | Leu | Asn | Val | Arg | Lys | Gly | His | Pro | Leu |
|  | 640 |  |  |  |  | 645 |  |  |  |  | 650 |

Figure 1f

| | | | | | | | | | | | |
|---|---|---|---|---|---|---|---|---|---|---|---|
| CTG | GTA | GCT | GTC | AAG | ATC | TTA | CGG | CCA | GAT | GCC | ACC |
| Leu | Val | Ala | Val | Lys | Ile | Leu | Arg | Pro | Asp | Ala | Thr |
| | | | 655 | | | | | 660 | | | |
| AAG | AAT | GCC | AGG | AAT | GAT | TTC | CTG | AAA | GAG | GTG | AAG |
| Lys | Asn | Ala | Arg | Asn | Asp | Phe | Leu | Lys | Glu | Val | Lys |
| | 665 | | | | | 670 | | | | | 675 |
| ATC | ATG | TCG | AGG | CTC | AAG | GAC | CCA | AAC | ATC | ATT | CGG |
| Ile | Met | Ser | Arg | Leu | Lys | Asp | Pro | Asn | Ile | Ile | Arg |
| | | | | 680 | | | | | 685 | | |
| CTG | CTG | GGC | GTG | TGT | GTG | CAG | GAC | GAC | CCC | CTC | TGC |
| Leu | Leu | Gly | Val | Cys | Val | Gln | Asp | Asp | Pro | Leu | Cys |
| | | 690 | | | | | 695 | | | | |
| ATG | ATT | ACT | GAC | TAC | ATG | GAG | AAC | GGC | GAC | CTC | AAC |
| Met | Ile | Thr | Asp | Tyr | Met | Glu | Asn | Gly | Asp | Leu | Asn |
| 700 | | | | | 705 | | | | | 710 | |
| CAG | TTC | CTC | AGT | GCC | CAC | CAG | CTG | GAG | GAC | AAG | GCA |
| Gln | Phe | Leu | Ser | Ala | His | Gln | Leu | Glu | Asp | Lys | Ala |
| | | | 715 | | | | | 720 | | | |
| GCC | GAG | GGG | GCC | CCT | GGG | GAC | GGG | CAG | GCT | GCG | CAG |
| Ala | Glu | Gly | Ala | Pro | Gly | Asp | Gly | Gln | Ala | Ala | Gln |
| | 725 | | | | | 730 | | | | | 735 |
| GGG | CCC | ACC | ATC | AGC | TAC | CCA | ATG | CTG | CTG | CAT | GTG |
| Gly | Pro | Thr | Ile | Ser | Tyr | Pro | Met | Leu | Leu | His | Val |
| | | | | 740 | | | | | 745 | | |
| GCA | GCC | CAG | ATC | GCC | TCC | GGC | ATG | CGC | TAT | CTG | GCC |
| Ala | Ala | Gln | Ile | Ala | Ser | Gly | Met | Arg | Tyr | Leu | Ala |
| | | | 750 | | | | | 755 | | | |
| ACA | CTC | AAC | TTT | GTA | CAT | CGG | GAC | CTG | GCC | ACG | CGG |
| Thr | Leu | Asn | Phe | Val | His | Arg | Asp | Leu | Ala | Thr | Arg |
| 760 | | | | | 765 | | | | | 770 | |
| AAC | TGC | CTA | GTT | GGG | GAA | AAT | TTC | ACC | ATC | AAA | ATC |
| Asn | Cys | Leu | Val | Gly | Glu | Asn | Phe | Thr | Ile | Lys | Ile |
| | | | 775 | | | | | 780 | | | |

Figure 1g

| GCA | GAC | TTT | GGC | ATG | AGC | CGG | AAC | CTC | TAT | GCT | GGG |
|---|---|---|---|---|---|---|---|---|---|---|---|
| Ala | Asp | Phe | Gly | Met | Ser | Arg | Asn | Leu | Tyr | Ala | Gly |
|   |   | 785 |   |   |   |   | 790 |   |   |   |   |

| GAC | TAT | TAC | CGT | GTG | CAG | GGC | CGG | GCA | GTG | CTG | CCC |
|---|---|---|---|---|---|---|---|---|---|---|---|
| Asp | Tyr | Tyr | Arg | Val | Gln | Gly | Arg | Ala | Val | Leu | Pro |
| 795 |   |   |   |   | 800 |   |   |   |   | 805 |   |

| ATC | CGC | TGG | ATG | GCC | TGG | GAG | TGC | ATC | CTC | ATG | GGG |
|---|---|---|---|---|---|---|---|---|---|---|---|
| Ile | Arg | Trp | Met | Ala | Trp | Glu | Cys | Ile | Leu | Met | Gly |
|   |   |   | 810 |   |   |   |   | 815 |   |   |   |

| AAG | TTC | ACG | ACT | GCG | AGT | GAC | GTG | TGG | GCC | TTT | GGT |
|---|---|---|---|---|---|---|---|---|---|---|---|
| Lys | Phe | Thr | Thr | Ala | Ser | Asp | Val | Trp | Ala | Phe | Gly |
|   | 820 |   |   |   |   | 825 |   |   |   |   | 830 |

| GTG | ACC | CTG | TGG | GAG | GTG | CTG | ATG | CTC | TGT | AGG | GCC |
|---|---|---|---|---|---|---|---|---|---|---|---|
| Val | Thr | Leu | Trp | Glu | Val | Leu | Met | Leu | Cys | Arg | Ala |
|   |   |   |   | 835 |   |   |   |   | 840 |   |   |

| CAG | CCC | TTT | GGG | CAG | CTC | ACC | GAC | GAG | CAG | GTC | ATC |
|---|---|---|---|---|---|---|---|---|---|---|---|
| Gln | Pro | Phe | Gly | Gln | Leu | Thr | Asp | Glu | Gln | Val | Ile |
|   |   | 845 |   |   |   |   | 850 |   |   |   |   |

| GAG | AAC | GCG | GGG | GAG | TTC | TTC | CGG | GAC | CAG | GGC | CGG |
|---|---|---|---|---|---|---|---|---|---|---|---|
| Glu | Asn | Ala | Gly | Glu | Phe | Phe | Arg | Asp | Gln | Gly | Arg |
| 855 |   |   |   |   | 860 |   |   |   |   | 865 |   |

| CAG | GTG | TAC | CTG | TCC | CGG | CCG | CCT | GCC | TGC | CCG | CAG |
|---|---|---|---|---|---|---|---|---|---|---|---|
| Gln | Val | Tyr | Leu | Ser | Arg | Pro | Pro | Ala | Cys | Pro | Gln |
|   |   |   | 870 |   |   |   |   | 875 |   |   |   |

| GGC | CTA | TAT | GAG | CTG | ATG | CTT | CGG | TGC | TGG | AGC | CGG |
|---|---|---|---|---|---|---|---|---|---|---|---|
| Gly | Leu | Tyr | Glu | Leu | Met | Leu | Arg | Cys | Trp | Ser | Arg |
|   | 880 |   |   |   |   | 885 |   |   |   |   | 890 |

| GAG | TCT | GAG | CAG | CGA | CCA | CCC | TTT | TCC | CAG | CTG | CAT |
|---|---|---|---|---|---|---|---|---|---|---|---|
| Glu | Ser | Glu | Gln | Arg | Pro | Pro | Phe | Ser | Gln | Leu | His |
|   |   |   |   | 895 |   |   |   |   | 900 |   |   |

| CGG | TTC | CTG | GCA | GAG | GAT | GCA | CTC | AAC | ACG | GTG | TGA |
|---|---|---|---|---|---|---|---|---|---|---|---|
| Arg | Phe | Leu | Ala | Glu | Asp | Ala | Leu | Asn | Thr | Val | End |
|   |   | 905 |   |   |   |   | 910 |   |   |   |   |

Figure 1h

| | | | |
|---|---|---|---|
| ATCACACATC | CAGCTGCCCC | TCCCTCAGGG | AGCGATCCAG |
| GGGAAGCCAG | TGACACTAAA | ACAAGAGGAC | ACAATGGCAC |
| CTCTGCCCCT | TCCCCTCCCG | ACAGCCATC | ACCTCTAATA |
| GAGGCAGTGA | GACTGCAGGC | TGGGCCCACC | CAGGGAGCTG |
| ATGCCCCTTC | TCCCCTTCCT | GGACACACTC | TCATGTCCCC |
| TTCCTGTTCT | TCCTTCCTAG | AAGCCCTGT | CGCCCACCCA |
| GCTGGTCCTG | TGGATGGGAT | CCTCTCCACC | CACCTCTAGC |
| CATCCCTTGG | GGAAGGGTGG | GGAGAAATAT | AGGATAGACA |
| CTGGACATGG | CCCATTGGAG | CACCTGGGCC | CCACTGGACA |
| ACACTGATTC | CTGGACAGGT | GGCTGCGCCC | CCAGCTTCTC |
| TCTCCCTGTC | ACACACTGGA | CCCCACTGGC | TGAGAATCTG |
| GGGGTGAGGA | GGACAAGAAG | GAGAGGAAAA | TGTTTCCTTG |
| TGCCTGCTCC | TGTACTTGTC | CTCAGCTTGG | GCTTCTTCCT |
| CCTCCATCAC | CTGAAACACT | GGACCTGGGG | GTAGCCCCGC |
| CCCAGCCCTC | AGTCACCCCC | CACTTCCCAC | CTGCAGTCTT |
| GTAGCTAGAA | CTTCTCTAAG | CCTATACGTT | TCTGTGGAGT |
| AAATATTGGG | ATTGGGGGGA | AAGAGGGAGC | AACGGCCCAT |
| AGCCTTGGGG | TTGGACATCT | CTAGTGTAGC | TGCCACATTG |
| ATTTTTCTAT | AATCACTTGG | GTTTGTACAT | TTTTGGGGGG |
| AGAGACACAG | ATTTTTACAC | TAATATATGG | ACCTAGCTTG |
| AGGCAATTTT | AATCCCTGC | ACTAGGCAGG | TAATAATAAA |
| GGTTGAGTTT | TCCACAAAAA | AAAAAAAA | |

Figure 4
a b c d e f g h i j k l m n
9.5 –
7.5 –
4.4 –
2.4 –
1.3 –
 – DDR
 – GAPDH

SEQUENCE LISTING

```
<160> NUMBER OF SEQ ID NOS: 6

<210> SEQ ID NO 1
<211> LENGTH: 3751
<212> TYPE: DNA
<213> ORGANISM: Homo sapiens
<220> FEATURE:
<221> NAME/KEY: CDS
<222> LOCATION: (142)..(2880)
<221> NAME/KEY: sig_peptide
<222> LOCATION: (1)..(195)
<223> OTHER INFORMATION: discoidin domain receptor (DDR) tyrosine kinase

<400> SEQUENCE: 1
cccgggtcgg accgcctggg tctgccggga agagcgatga gaggtgtctg aaggtggcta         60
ttcactgagc gatggggttg gacttgaagg aatgccaaga gatgctgccc ccacccctt        120 aggcccgagg gatcaggagc t atg gga cca gag gcc ctg tca tct tta ctg        171
              Met Gly Pro Glu Ala Leu Ser Ser Leu Leu
                1               5                  10 ctg ctg ctc ttg gtg gca agt gga gat gct gac atg aag gga cat ttt        219
Leu Leu Leu Leu Val Ala Ser Gly Asp Ala Asp Met Lys Gly His Phe
              15                  20                  25 gat cct gcc aag tgc cgc tat gcc ctg ggc atg cag gac cgg acc atc        267
Asp Pro Ala Lys Cys Arg Tyr Ala Leu Gly Met Gln Asp Arg Thr Ile
```

-continued

| | 30 | | | | 35 | | | | 40 | | | | |
|---|---|---|---|---|---|---|---|---|---|---|---|---|---|
| cca | gac | agt | gac | atc | tct | gct | tcc | agc | tcc | tgg | tca | gat tcc act gcc | 315 |
| Pro | Asp | Ser | Asp | Ile | Ser | Ala | Ser | Ser | Ser | Trp | Ser | Asp Ser Thr Ala | |
| | | | 45 | | | | 50 | | | | 55 | | |
| gcc | cgc | cac | agc | agg | ttg | gag | agc | agt | gac | ggg | gat | ggg gcc tgg tgc | 363 |
| Ala | Arg | His | Ser | Arg | Leu | Glu | Ser | Ser | Asp | Gly | Asp | Gly Ala Trp Cys | |
| | 60 | | | | 65 | | | | 70 | | | | |
| ccc | gca | ggg | tcg | gtg | ttt | ccc | aag | gag | gag | gag | tac | ttg cag gtg gat | 411 |
| Pro | Ala | Gly | Ser | Val | Phe | Pro | Lys | Glu | Glu | Glu | Tyr | Leu Gln Val Asp | |
| 75 | | | | 80 | | | | 85 | | | | 90 | |
| cta | caa | cga | ctc | cac | ctg | gtg | gct | ctg | gtg | ggc | acc | cag gga cgg cat | 459 |
| Leu | Gln | Arg | Leu | His | Leu | Val | Ala | Leu | Val | Gly | Thr | Gln Gly Arg His | |
| | | | | 95 | | | | 100 | | | | 105 | |
| gcc | ggg | ggc | ctg | ggc | aag | gag | ttc | tcc | cgg | agc | tac | cgg ctc cgt tac | 507 |
| Ala | Gly | Gly | Leu | Gly | Lys | Glu | Phe | Ser | Arg | Ser | Tyr | Arg Leu Arg Tyr | |
| | | | 110 | | | | 115 | | | | 120 | | |
| tcc | cgg | gat | ggt | cgc | cgc | tgg | atg | ggc | tgg | aag | gac | cgc tgg ggt cag | 555 |
| Ser | Arg | Asp | Gly | Arg | Arg | Trp | Met | Gly | Trp | Lys | Asp | Arg Trp Gly Gln | |
| | | 125 | | | | 130 | | | | 135 | | | |
| gag | gtg | atc | tca | ggc | aat | gag | gac | cct | gag | gga | gtg | gtg ctg aag gac | 603 |
| Glu | Val | Ile | Ser | Gly | Asn | Glu | Asp | Pro | Glu | Gly | Val | Val Leu Lys Asp | |
| | 140 | | | | 145 | | | | 150 | | | | |
| ctt | ggg | ccc | ccc | atg | gtt | gcc | cga | ctg | gtt | cgc | ttc | tac ccc cgg gct | 651 |
| Leu | Gly | Pro | Pro | Met | Val | Ala | Arg | Leu | Val | Arg | Phe | Tyr Pro Arg Ala | |
| 155 | | | | 160 | | | | 165 | | | | 170 | |
| gac | cgg | gtc | atg | agc | gtc | tgt | ctg | cgg | gta | gag | ctc | tat ggc tgc ctc | 699 |
| Asp | Arg | Val | Met | Ser | Val | Cys | Leu | Arg | Val | Glu | Leu | Tyr Gly Cys Leu | |
| | | | | 175 | | | | 180 | | | | 185 | |
| tgg | agg | gat | gga | ctc | ctg | tct | tac | acc | gcc | cct | gtg | ggg cag aca atg | 747 |
| Trp | Arg | Asp | Gly | Leu | Leu | Ser | Tyr | Thr | Ala | Pro | Val | Gly Gln Thr Met | |
| | | | 190 | | | | 195 | | | | 200 | | |
| tat | tta | tct | gag | gcc | gtg | tac | ctc | aac | gac | tcc | acc | tat gac gga cat | 795 |
| Tyr | Leu | Ser | Glu | Ala | Val | Tyr | Leu | Asn | Asp | Ser | Thr | Tyr Asp Gly His | |
| | | 205 | | | | 210 | | | | 215 | | | |
| acc | gtg | ggc | gga | ctg | cag | tat | ggg | ggt | ctg | ggc | cag | ctg gca gat ggt | 843 |
| Thr | Val | Gly | Gly | Leu | Gln | Tyr | Gly | Gly | Leu | Gly | Gln | Leu Ala Asp Gly | |
| | 220 | | | | 225 | | | | 230 | | | | |
| gtg | gtg | ggg | ctg | gat | gac | ttt | agg | aag | agt | cag | gag | ctg cgg gtc tgg | 891 |
| Val | Val | Gly | Leu | Asp | Asp | Phe | Arg | Lys | Ser | Gln | Glu | Leu Arg Val Trp | |
| 235 | | | | 240 | | | | 245 | | | | 250 | |
| cca | ggc | tat | gac | tat | gtg | gga | tgg | agc | aac | cac | agc | ttc tcc agt ggc | 939 |
| Pro | Gly | Tyr | Asp | Tyr | Val | Gly | Trp | Ser | Asn | His | Ser | Phe Ser Ser Gly | |
| | | | 255 | | | | 260 | | | | 265 | | |
| tat | gtg | gag | atg | gag | ttt | gag | ttt | gac | cgg | ctg | agg | gcc ttc cag gct | 987 |
| Tyr | Val | Glu | Met | Glu | Phe | Glu | Phe | Asp | Arg | Leu | Arg | Ala Phe Gln Ala | |
| | | | 270 | | | | 275 | | | | 280 | | |
| atg | cag | gtc | cac | tgt | aac | aac | atg | cac | acg | ctg | gga | gcc cgt ctg cct | 1035 |
| Met | Gln | Val | His | Cys | Asn | Asn | Met | His | Thr | Leu | Gly | Ala Arg Leu Pro | |
| | | 285 | | | | 290 | | | | 295 | | | |
| ggc | ggg | gtg | gaa | tgt | cgc | ttc | cgg | cgt | ggc | cct | gcc | atg gcc tgg gag | 1083 |
| Gly | Gly | Val | Glu | Cys | Arg | Phe | Arg | Arg | Gly | Pro | Ala | Met Ala Trp Glu | |
| | 300 | | | | 305 | | | | 310 | | | | |
| ggg | gag | ccc | atg | cgc | cac | aac | cta | ggg | ggc | aac | ctg | ggg gac ccc aga | 1131 |
| Gly | Glu | Pro | Met | Arg | His | Asn | Leu | Gly | Gly | Asn | Leu | Gly Asp Pro Arg | |
| 315 | | | | 320 | | | | 325 | | | | 330 | |
| gcc | cgg | gct | gtc | tca | gtg | ccc | ctt | ggc | ggc | cgt | gtg | gct cgc ttt ctg | 1179 |
| Ala | Arg | Ala | Val | Ser | Val | Pro | Leu | Gly | Gly | Arg | Val | Ala Arg Phe Leu | |
| | | | | 335 | | | | 340 | | | | 345 | |
| cag | tgc | cgc | ttc | ctc | ttt | gcg | ggg | ccc | tgg | tta | ctc | ttc agc gaa atc | 1227 |

-continued

```
Gln Cys Arg Phe Leu Phe Ala Gly Pro Trp Leu Leu Phe Ser Glu Ile
            350                 355                 360 tcc ttc atc tct gat gtg gtg aac aat tcc tct ccg gca ctg gga ggc    1275
Ser Phe Ile Ser Asp Val Val Asn Asn Ser Ser Pro Ala Leu Gly Gly
        365                 370                 375 acc ttc ccg cca gcc ccc tgg tgg ccg cct ggc cca cct ccc acc aac    1323
Thr Phe Pro Pro Ala Pro Trp Trp Pro Pro Gly Pro Pro Pro Thr Asn
    380                 385                 390 ttc agc agc ttg gag ctg gag ccc aga ggc cag cag ccc gtg gcc aag    1371
Phe Ser Ser Leu Glu Leu Glu Pro Arg Gly Gln Gln Pro Val Ala Lys
395                 400                 405                 410 gcc gag ggg agc ccg acc gcc atc ctc atc ggc tgc ctg gtg gcc atc    1419
Ala Glu Gly Ser Pro Thr Ala Ile Leu Ile Gly Cys Leu Val Ala Ile
                415                 420                 425 atc ctg ctc ctg ctg ctc att gcc ctc atg ctc tgg cgg ctg cac        1467
Ile Leu Leu Leu Leu Leu Ile Ile Ala Leu Met Leu Trp Arg Leu His
            430                 435                 440 tgg cgc agg ctc ctc agc aag gct gaa cgg agg gtg ttg gaa gag gag    1515
Trp Arg Arg Leu Leu Ser Lys Ala Glu Arg Arg Val Leu Glu Glu Glu
        445                 450                 455 ctg acg gtt cac ctc tct gtc cct ggg gac act atc ctc atc aac aac    1563
Leu Thr Val His Leu Ser Val Pro Gly Asp Thr Ile Leu Ile Asn Asn
    460                 465                 470 cgc cca ggt cct aga gag cca ccc ccg tac cag gag ccc cgg cct cgt    1611
Arg Pro Gly Pro Arg Glu Pro Pro Pro Tyr Gln Glu Pro Arg Pro Arg
475                 480                 485                 490 ggg aat ccg ccc cac tcc gct ccc tgt gtc ccc aat ggc tct gcg ttg    1659
Gly Asn Pro Pro His Ser Ala Pro Cys Val Pro Asn Gly Ser Ala Leu
                495                 500                 505 ctg ctc tcc aat cca gcc tac cgc ctc ctt ctg gcc act tac gcc cgt    1707
Leu Leu Ser Asn Pro Ala Tyr Arg Leu Leu Leu Ala Thr Tyr Ala Arg
            510                 515                 520 ccc cct cga ggc ccg ggc ccc ccc aca ccc gcc tgg gcc aaa ccc acc    1755
Pro Pro Arg Gly Pro Gly Pro Pro Thr Pro Ala Trp Ala Lys Pro Thr
        525                 530                 535 aac acc cag gcc tac agt ggg gac tat atg gag cct gag aag cca ggc    1803
Asn Thr Gln Ala Tyr Ser Gly Asp Tyr Met Glu Pro Glu Lys Pro Gly
    540                 545                 550 gcc ccg ctt ctg ccc cca cct ccc cag aac agc gtc ccc cat tat gcc    1851
Ala Pro Leu Leu Pro Pro Pro Pro Gln Asn Ser Val Pro His Tyr Ala
555                 560                 565                 570 gag gct gac att gtt acc ctg cag ggc gtc acc ggg ggc aac acc tat    1899
Glu Ala Asp Ile Val Thr Leu Gln Gly Val Thr Gly Gly Asn Thr Tyr
                575                 580                 585 gct gtg cct gca cct ccc cca ggg gca gtc ggg gat ggg ccc ccc aga    1947
Ala Val Pro Ala Pro Pro Pro Gly Ala Val Gly Asp Gly Pro Pro Arg
            590                 595                 600 gtg gat ttc cct cga tct cga ctc cgc ttc aag gag aag ctt ggc gag    1995
Val Asp Phe Pro Arg Ser Arg Leu Arg Phe Lys Glu Lys Leu Gly Glu
        605                 610                 615 ggc cag ttt ggg gag gtg cac ctg tgt gag gtc gac agc cct caa gat    2043
Gly Gln Phe Gly Glu Val His Leu Cys Glu Val Asp Ser Pro Gln Asp
    620                 625                 630 ctg gtt agt ctt gat ttc ccc ctt aat gtg cgt aag gga cac cct ttg    2091
Leu Val Ser Leu Asp Phe Pro Leu Asn Val Arg Lys Gly His Pro Leu
635                 640                 645                 650 ctg gta gct gtc aag atc tta cgg cca gat gcc acc aag aat gcc agg    2139
Leu Val Ala Val Lys Ile Leu Arg Pro Asp Ala Thr Lys Asn Ala Arg
                655                 660                 665
```

-continued

| | |
|---|---|
| aat gat ttc ctg aaa gag gtg aag atc atg tcg agg ctc aag gac cca<br>Asn Asp Phe Leu Lys Glu Val Lys Ile Met Ser Arg Leu Lys Asp Pro<br>           670                 675               680 | 2187 |
| aac atc att cgg ctg ctg ggc gtg tgt gtg cag gac gac ccc ctc tgc<br>Asn Ile Ile Arg Leu Leu Gly Val Cys Val Gln Asp Asp Pro Leu Cys<br>           685                 690               695 | 2235 |
| atg att act gac tac atg gag aac ggc gac ctc aac cag ttc ctc agt<br>Met Ile Thr Asp Tyr Met Glu Asn Gly Asp Leu Asn Gln Phe Leu Ser<br>700                 705                 710 | 2283 |
| gcc cac cag ctg gag gac aag gca gcc gag ggg gcc cct ggg gac ggg<br>Ala His Gln Leu Glu Asp Lys Ala Ala Glu Gly Ala Pro Gly Asp Gly<br>715                 720                 725               730 | 2331 |
| cag gct gcg cag ggg ccc acc atc agc tac cca atg ctg ctg cat gtg<br>Gln Ala Ala Gln Gly Pro Thr Ile Ser Tyr Pro Met Leu Leu His Val<br>           735                 740               745 | 2379 |
| gca gcc cag atc gcc tcc ggc atg cgc tat ctg gcc aca ctc aac ttt<br>Ala Ala Gln Ile Ala Ser Gly Met Arg Tyr Leu Ala Thr Leu Asn Phe<br>           750                 755               760 | 2427 |
| gta cat cgg gac ctg gcc acg cgg aac tgc cta gtt ggg gaa aat ttc<br>Val His Arg Asp Leu Ala Thr Arg Asn Cys Leu Val Gly Glu Asn Phe<br>765                 770                 775 | 2475 |
| acc atc aaa atc gca gac ttt ggc atg agc cgg aac ctc tat gct ggg<br>Thr Ile Lys Ile Ala Asp Phe Gly Met Ser Arg Asn Leu Tyr Ala Gly<br>           780                 785               790 | 2523 |
| gac tat tac cgt gtg cag ggc cgg gca gtg ctg ccc atc cgc tgg atg<br>Asp Tyr Tyr Arg Val Gln Gly Arg Ala Val Leu Pro Ile Arg Trp Met<br>795                 800                 805               810 | 2571 |
| gcc tgg gag tgc atc ctc atg ggg aag ttc acg act gcg agt gac gtg<br>Ala Trp Glu Cys Ile Leu Met Gly Lys Phe Thr Thr Ala Ser Asp Val<br>           815                 820               825 | 2619 |
| tgg gcc ttt ggt gtg acc ctg tgg gag gtg ctg atg ctc tgt agg gcc<br>Trp Ala Phe Gly Val Thr Leu Trp Glu Val Leu Met Leu Cys Arg Ala<br>           830                 835               840 | 2667 |
| cag ccc ttt ggg cag ctc acc gac gag cag gtc atc gag aac gcg ggg<br>Gln Pro Phe Gly Gln Leu Thr Asp Glu Gln Val Ile Glu Asn Ala Gly<br>           845                 850               855 | 2715 |
| gag ttc ttc cgg gac cag ggc cgg cag gtg tac ctg tcc cgg ccg cct<br>Glu Phe Phe Arg Asp Gln Gly Arg Gln Val Tyr Leu Ser Arg Pro Pro<br>860                 865                 870 | 2763 |
| gcc tgc ccg cag ggc cta tat gag ctg atg ctt cgg tgc tgg agc cgg<br>Ala Cys Pro Gln Gly Leu Tyr Glu Leu Met Leu Arg Cys Trp Ser Arg<br>875                 880                 885               890 | 2811 |
| gag tct gag cag cga cca ccc ttt tcc cag ctg cat cgg ttc ctg gca<br>Glu Ser Glu Gln Arg Pro Pro Phe Ser Gln Leu His Arg Phe Leu Ala<br>           895                 900               905 | 2859 |
| gag gat gca ctc aac acg gtg tga atcacacatc cagctgcccc tccctcaggg<br>Glu Asp Ala Leu Asn Thr Val<br>           910 | 2913 |
| agcgatccag gggaagccag tgacactaaa acaagaggac acaatggcac ctctgcccct | 2973 |
| tcccctcccg acagcccatc acctctaata gaggcagtga gactgcaggc tgggcccacc | 3033 |
| cagggagctg atgccccttc tcccttcct ggacacactc tcatgtcccc ttcctgttct | 3093 |
| tccttcctag aagcccctgt cgcccaccca gctggtcctg tggatgggat cctctccacc | 3153 |
| cacctctagc catcccttgg ggaagggtgg ggagaaatat aggatagaca ctggacatgg | 3213 |
| cccattggag cacctgggcc ccactggaca acactgattc ctggacaggt ggctgcgccc | 3273 |
| ccagcttctc tctccctgtc acacactgga ccccactggc tgagaatctg ggggtgagga | 3333 |
| ggacaagaag gagaggaaaa tgtttccttg tgcctgctcc tgtacttgtc ctcagcttgg | 3393 |

```
gcttcttcct cctccatcac ctgaaacact ggacctgggg gtagcccgc cccagccctc    3453 agtcacccc cacttcccac ctgcagtctt gtagctagaa cttctctaag cctatacgtt    3513
tctgtggagt aaatattggg attgggggga aagagggagc aacggcccat agccttgggg   3573
ttggacatct ctagtgtagc tgccacattg atttttctat aatcacttgg gtttgtacat   3633
ttttgggggg agagacacag attttacac taatatatg acctagcttg aggcaatttt     3693
aatcccctgc actaggcagg taataataaa ggttgagttt tccacaaaaa aaaaaaa      3751
```

<210> SEQ ID NO 2
<211> LENGTH: 913
<212> TYPE: PRT
<213> ORGANISM: Homo sapiens
<220> FEATURE:
<223> OTHER INFORMATION: discoidin domain receptor (DDR) tyrosine kinase
<221> NAME/KEY: PEPTIDE
<222> LOCATION: (1)..(18)
<223> OTHER INFORMATION: signal peptide
<221> NAME/KEY: SITE
<222> LOCATION: (19)..(24)
<223> OTHER INFORMATION: uncertain point of signal peptide cleavage
      between amino acids 19 to 24
<221> NAME/KEY: DOMAIN
<222> LOCATION: (31)..(185)
<223> OTHER INFORMATION: discoidin I-type domain
<221> NAME/KEY: SITE
<222> LOCATION: (374)..(415)
<223> OTHER INFORMATION: proline/glycine-rich portion of connecting
      region interrupted by transmembrane domain
<221> NAME/KEY: TRANSMEM
<222> LOCATION: (417)..(439)
<223> OTHER INFORMATION: transmembrane domain
<221> NAME/KEY: SITE
<222> LOCATION: (466)..(601)
<223> OTHER INFORMATION: proline/glycine-rich portion of connecting
      region interrupted by transmembrane domain
<221> NAME/KEY: TURN
<222> LOCATION: (510)..(513)
<223> OTHER INFORMATION: tight turn recognition motif for
      internalization in coated pits
<221> NAME/KEY: DOMAIN
<222> LOCATION: (616)..(905)
<223> OTHER INFORMATION: tyrosine kinase domain

<400> SEQUENCE: 2

Met Gly Pro Glu Ala Leu Ser Ser Leu Leu Leu Leu Leu Leu Val Ala
 1               5                  10                  15

Ser Gly Asp Ala Asp Met Lys Gly His Phe Asp Pro Ala Lys Cys Arg
            20                  25                  30

Tyr Ala Leu Gly Met Gln Asp Arg Thr Ile Pro Asp Ser Asp Ile Ser
        35                  40                  45

Ala Ser Ser Ser Trp Ser Asp Ser Thr Ala Ala Arg His Ser Arg Leu
    50                  55                  60

Glu Ser Ser Asp Gly Asp Gly Ala Trp Cys Pro Ala Gly Ser Val Phe
65                  70                  75                  80

Pro Lys Glu Glu Glu Tyr Leu Gln Val Asp Leu Gln Arg Leu His Leu
                85                  90                  95

Val Ala Leu Val Gly Thr Gln Gly Arg His Ala Gly Gly Leu Gly Lys
            100                 105                 110

Glu Phe Ser Arg Ser Tyr Arg Leu Arg Tyr Ser Arg Asp Gly Arg Arg
        115                 120                 125

Trp Met Gly Trp Lys Asp Arg Trp Gly Gln Glu Val Ile Ser Gly Asn
    130                 135                 140

Glu Asp Pro Glu Gly Val Val Leu Lys Asp Leu Gly Pro Pro Met Val

```
                                   -continued 145                 150                 155                 160
Ala Arg Leu Val Arg Phe Tyr Pro Arg Ala Asp Arg Val Met Ser Val
                165                 170                 175

Cys Leu Arg Val Glu Leu Tyr Gly Cys Leu Trp Arg Asp Gly Leu Leu
                180                 185                 190

Ser Tyr Thr Ala Pro Val Gly Gln Thr Met Tyr Leu Ser Glu Ala Val
                195                 200                 205

Tyr Leu Asn Asp Ser Thr Tyr Asp Gly His Thr Val Gly Gly Leu Gln
                210                 215                 220

Tyr Gly Gly Leu Gly Gln Leu Ala Asp Gly Val Val Gly Leu Asp Asp
225                 230                 235                 240

Phe Arg Lys Ser Gln Glu Leu Arg Val Trp Pro Gly Tyr Asp Tyr Val
                245                 250                 255

Gly Trp Ser Asn His Ser Phe Ser Ser Gly Tyr Val Glu Met Glu Phe
                260                 265                 270

Glu Phe Asp Arg Leu Arg Ala Phe Gln Ala Met Gln Val His Cys Asn
                275                 280                 285

Asn Met His Thr Leu Gly Ala Arg Leu Pro Gly Gly Val Glu Cys Arg
                290                 295                 300

Phe Arg Arg Gly Pro Ala Met Ala Trp Glu Gly Glu Pro Met Arg His
305                 310                 315                 320

Asn Leu Gly Gly Asn Leu Gly Asp Pro Arg Ala Arg Ala Val Ser Val
                325                 330                 335

Pro Leu Gly Gly Arg Val Ala Arg Phe Leu Gln Cys Arg Phe Leu Phe
                340                 345                 350

Ala Gly Pro Trp Leu Leu Phe Ser Glu Ile Ser Phe Ile Ser Asp Val
                355                 360                 365

Val Asn Asn Ser Ser Pro Ala Leu Gly Gly Thr Phe Pro Pro Ala Pro
370                 375                 380

Trp Trp Pro Pro Gly Pro Pro Thr Asn Phe Ser Ser Leu Glu Leu
385                 390                 395                 400

Glu Pro Arg Gly Gln Gln Pro Val Ala Lys Ala Glu Gly Ser Pro Thr
                405                 410                 415

Ala Ile Leu Ile Gly Cys Leu Val Ala Ile Ile Leu Leu Leu Leu Leu
                420                 425                 430

Ile Ile Ala Leu Met Leu Trp Arg Leu His Trp Arg Arg Leu Leu Ser
                435                 440                 445

Lys Ala Glu Arg Arg Val Leu Glu Glu Glu Leu Thr Val His Leu Ser
                450                 455                 460

Val Pro Gly Asp Thr Ile Leu Ile Asn Asn Arg Pro Gly Pro Arg Glu
465                 470                 475                 480

Pro Pro Pro Tyr Gln Glu Pro Arg Pro Arg Gly Asn Pro Pro His Ser
                485                 490                 495

Ala Pro Cys Val Pro Asn Gly Ser Ala Leu Leu Leu Ser Asn Pro Ala
                500                 505                 510

Tyr Arg Leu Leu Leu Ala Thr Tyr Ala Arg Pro Pro Arg Gly Pro Gly
                515                 520                 525

Pro Pro Thr Pro Ala Trp Ala Lys Pro Thr Asn Thr Gln Ala Tyr Ser
                530                 535                 540

Gly Asp Tyr Met Glu Pro Glu Lys Pro Gly Ala Pro Leu Leu Pro Pro
545                 550                 555                 560

Pro Pro Gln Asn Ser Val Pro His Tyr Ala Glu Ala Asp Ile Val Thr
                565                 570                 575
```

```
Leu Gln Gly Val Thr Gly Gly Asn Thr Tyr Ala Val Pro Ala Pro Pro
            580                 585                 590

Pro Gly Ala Val Gly Asp Gly Pro Pro Arg Val Asp Phe Pro Arg Ser
        595                 600                 605

Arg Leu Arg Phe Lys Glu Lys Leu Gly Glu Gly Gln Phe Gly Glu Val
        610                 615                 620

His Leu Cys Glu Val Asp Ser Pro Gln Asp Leu Val Ser Leu Asp Phe
625                 630                 635                 640

Pro Leu Asn Val Arg Lys Gly His Pro Leu Leu Val Ala Val Lys Ile
                645                 650                 655

Leu Arg Pro Asp Ala Thr Lys Asn Ala Arg Asn Asp Phe Leu Lys Glu
            660                 665                 670

Val Lys Ile Met Ser Arg Leu Lys Asp Pro Asn Ile Ile Arg Leu Leu
        675                 680                 685

Gly Val Cys Val Gln Asp Asp Pro Leu Cys Met Ile Thr Asp Tyr Met
        690                 695                 700

Glu Asn Gly Asp Leu Asn Gln Phe Leu Ser Ala His Gln Leu Glu Asp
705                 710                 715                 720

Lys Ala Ala Glu Gly Ala Pro Gly Asp Gly Gln Ala Ala Gln Gly Pro
                725                 730                 735

Thr Ile Ser Tyr Pro Met Leu Leu His Val Ala Ala Gln Ile Ala Ser
            740                 745                 750

Gly Met Arg Tyr Leu Ala Thr Leu Asn Phe Val His Arg Asp Leu Ala
        755                 760                 765

Thr Arg Asn Cys Leu Val Gly Glu Asn Phe Thr Ile Lys Ile Ala Asp
        770                 775                 780

Phe Gly Met Ser Arg Asn Leu Tyr Ala Gly Asp Tyr Tyr Arg Val Gln
785                 790                 795                 800

Gly Arg Ala Val Leu Pro Ile Arg Trp Met Ala Trp Glu Cys Ile Leu
                805                 810                 815

Met Gly Lys Phe Thr Thr Ala Ser Asp Val Trp Ala Phe Gly Val Thr
            820                 825                 830

Leu Trp Glu Val Leu Met Leu Cys Arg Ala Gln Pro Phe Gly Gln Leu
        835                 840                 845

Thr Asp Glu Gln Val Ile Glu Asn Ala Gly Glu Phe Phe Arg Asp Gln
850                 855                 860

Gly Arg Gln Val Tyr Leu Ser Arg Pro Pro Ala Cys Pro Gln Gly Leu
865                 870                 875                 880

Tyr Glu Leu Met Leu Arg Cys Trp Ser Arg Glu Ser Glu Gln Arg Pro
                885                 890                 895

Pro Phe Ser Gln Leu His Arg Phe Leu Ala Glu Asp Ala Leu Asn Thr
            900                 905                 910

Val

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: antisense
      oligonucleotide

<400> SEQUENCE: 3
gttscgrgcr gccagrtcsc grtg                                          24
```

```
<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: sequence
      found in the cytoplasmic juxtamembrane sequences of
      several plasma membrane receptors
<221> NAME/KEY: SITE
<222> LOCATION: (3)
<222> LOCATION: Xaa is any amino acid

<400> SEQUENCE: 4

Asn Pro Xaa Tyr
  1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: tight turn
      recognition motif for internalization in coated
      pits

<400> SEQUENCE: 5

Asn Pro Ala Tyr
  1

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: amino acid
      sequence found in many tyrosine kinases
      corresponding to the antisense oligonucleotide in
      SEQ ID NO:3

<400> SEQUENCE: 6

His Arg Asp Leu Ala Ala Arg Asn
  1               5
```

RECEPTOR TYROSINE KINASE WITH A DISCOIDIN-TYPE BINDING DOMAIN

This application is a continuation in part of and claims the benefit of U.S. application Ser. No. 08/292,299, filed Aug. 16, 1994 now abandoned which in turn is a continuation-in-part of application Ser. No. 08/077,254, filed Jun. 14, 1993, abandoned now the disclosures of which are incorporated by reference.

This invention was made with Government support under Grant No. DK37661, awarded by the National Institute of Health. The Government has certain rights in this invention.

BACKGROUND OF THE INVENTION

1. Field of the Invention

The present invention relates to receptor tyrosine kinases with discoidin-type or like binding domains and nucleic acids encoding such receptor tyrosine kinases. It is noted that the "type" or "like" term that is associated with the names discoidin, discoidin I, and equivalent molecules in this disclosure implies that structural and functional similarities exist between the subject molecule's binding domain and the binding domain found in discoidin, discoidin I, and equivalent molecules.

2. Description of the Background Art

Certain extracellular molecules influence cellular growth, differentiation or development via activation of receptor tyrosine kinases (Bishop, J. M. (1991) *Cell* 64, 235–248 and Hunter, T. (1991) *Meth. Enz.* 200, 3–37, which are incorporated herein by reference). Receptor tyrosine kinases are composed of an extracellular ligand binding domain and a cytoplasmic catalytic domain that allow for specific decoding of extracellular signals and initiation of intracellular biochemical effects. A large number of cDNAs for putative receptor tyrosine kinases have been cloned and sequenced (Hanks, S. K. & Quinn, A. M. (1991) *Meth. Enz.* 200, 38–62, which is incorporated herein by reference). With rare exception (Shier, P. & Watt, V. M. (1989) *J. Biol. Chem.* 264, 14605–14608, which is incorporated herein by reference), sequence similarities in extracellular domains have not suggested the type of ligand that might activate a given receptor. Nevertheless, the diversity of receptor tyrosine kinase extracellular domains implies that there are a large number of as yet unidentified extracellular molecules that can regulate receptor tyrosine kinase activity and, by extension, growth, differentiation or development. Identification of these ligands is crucial for a comprehensive understanding of these fundamental biological processes. It is clear that researchers are only beginning to understand the complexity of the extracellular signals that can activate receptor tyrosine kinases. Also, little is known about the fundamental process of information exchange across the membrane to initiate the intracellular cascade of biochemical effectors. Disclosed here is the cDNA cloning and characterization of a novel breast carcinoma cell protein with a primary structure which suggests that this protein is a receptor tyrosine kinase with an unusual mechanism of transmembrane signaling. An extracellular domain of this protein is similar to the lectin-like or type protein or specifically the carbohydrate-binding protein discoidin I.

SUMMARY OF THE INVENTION

An object of the present invention is to present a polypeptide having both a first domain with carbohydrate or discoidin I-type binding activity and a second domain with tyrosine kinase activity.

Another object of the present invention is to disclose a nucleic acid sequence that encodes for a polypeptide having a first domain with carbohydrate or discoidin I-type binding activity and a second domain with tyrosine kinase activity.

A further object of the present invention is to make known a marker that may be utilized to predict and diagnose tumors of the breast and lung.

Still another object of the present invention is to describe a nucleic acid sequence that encodes a polypeptide having both discoidin I-type ligand binding characteristics and tyrosine kinase activity that can be utilized in immunological and inhibitory regulation of associated tumors.

Yet a further object of the present invention is to disclose a polypeptide having both discoidin I-type ligand binding characteristics and tyrosine kinase activity that can be utilized in immunological and inhibitory regulation of associated tumors.

Disclosed is a novel breast carcinoma tyrosine phosphoprotein, DDR (Discoidin Domain Receptor), that defines a novel class of receptor tyrosine kinases. The DDR cDNA predicts a C-terminal tyrosine kinase domain and an N-terminal domain similar to the *Dictyostelium discoideum* lectin named discoidin or more specifically discoidin I. These domains are connected by an extraordinary hydrophilic proline/glycine-rich domain, which is interrupted by a predicted transmembrane sequence. This extended proline/glycine-rich region suggests an unusual geometry of interaction with ligand or substrates. Discoidin I-type domains are also found in other proteins, including coagulation factors V and VIII. Discoidin I-type domains may interact with specific cell surface molecules. SEQ ID NO: 1 designates the nucleotide sequence of the present invention, SEQ ID NO: 2 designates the polypepteide or protein sequence of the present invention, and SEQ ID NO: 3 designates the probe utilized in the subject invention.

Other objects, advantages, and novel features of the present invention will become apparent from the detailed description that follows, when considered in conjunction with the associated drawings.

DESCRIPTION OF THE FIGURES

FIGS. 1*a–h* (also, see SEQ ID NOS: 1 and 2) show the nucleotide and deduced amino acid sequence of the human DDR cDNA. Amino acids are numbered for the precursor protein. The single underlined amino acid sequence near the N-terminus contains the discoidin I-type domain and the single underlined amino acid sequence near the C-terminus contains the tyrosine kinase domain. The predicted signal peptide (1–18) and transmembrane (418–440) domains are in bold type. Uncertainty, as to the point of signal peptide cleavage, exists between amino acids 19 to 24. Potential N-glycosylation sites are bolded with underlining and cysteines within the extracellular region are marked with an asterisk. The proline and glycine residues between the discoidin I-type domain and the tyrosine kinase domain are italicized. The bolded with double underlining show the most proline/glycine-rich of the connecting region. The tyrosine within the Asn-Pro-Xaa-Tyr (SEQ ID NO:4) sequence found in the cytoplasmic juxtamembrane sequences of several plasma membrane receptors (Bansal, A. & Gierasch, L. M. (1991) *Cell* 67, 1195–201, which is incorporated herein by reference) is denoted with a double asterisk.

FIG. 4 shows a Northern analysis of DDR transcripts in mouse tissue RNAs. PolyA+RNAs from adult mouse tissues:a brain, b thymus, c lung, d heart, e liver, f spleen, g small intestine, h kidney, i pancreas, j skeletal muscle, k testis, I ovary, m uterus, n placenta were fractionated on formaldehyde agarose gels, transferred to a nitrocellulose filter and hybridized with a 3.7 kilobase $^{32}$P-labeled EcoR I fragment containing the DDR cDNA in 40% formamide at 42° C. After washing and exposure to film for 3 days, the filter was subsequently probed with a $^{32}$P-labeled mouse GAPDH cDNA to control for the amount of RNA loaded in each lane. The mobilities of RNA markers is indicated in kilobases. The migrations of the DDR and GAPDH (glyceraldehyde 3-phosphate dehydrogenase) transcripts are indicated.

DESCRIPTION OF THE PREFERRED EMBODIMENT

Figure 2:
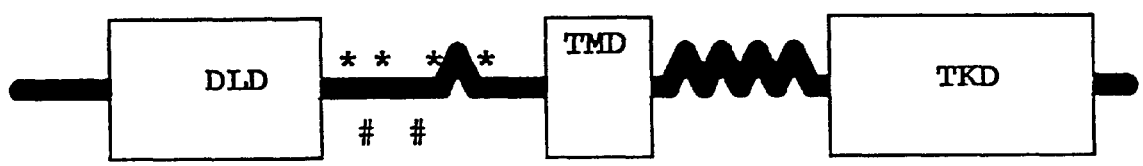
FIG. 2 is a schematic representation of DDR. DLD= discoidin I-type domain; TMD=transmembrane domain; TKD=tyrosine kinase domain. The kinked line represents the extent of the most proline/glycine-rich portion of the connecting region. The approximate boundaries of the peptide fused to b-galactosidase for rabbit immunization are indicated by #. The approximate positions of potential sites of N-glycosylation are denoted by asterisks.

The DDR cDNA was isolated during a search for tyrosine kinase cDNAs related to those in the insulin receptor family. This cDNA predicts a protein of 914 amino acids (105 kDa) that has a signal peptide and a transmembrane domain (FIGS. 1 and 2). The predicted DDR protein also has the following features: a discoidin I-type domain near the N-terminus, an extensive proline/glycine-rich region between the discoidin I-type domain and the transmembrane domain, and another extensive proline/glycine-rich region between the transmembrane domain and the C-terminal tyrosine kinase domain. The sequence of the DDR catalytic domain places it within the insulin receptor family of receptor tyrosine kinases (Hanks, S. K. & Quinn, A. M. (1991) *Meth. Enz.* 200, 38–62, which is incorporated herein by reference). The catalytic domain is 45% identical with the trkA protein catalytic domain (Martin-Zanca, D., Oskam, R., Mitra, G., Copeland, T. & Barbacid, M. (1989) *Mol. Cell. Biol.* 9, 24–33, which is incorporated herein by reference) but the remainder of the molecule has no similarity to any other portion of the trk proteins. Also like trkA, the DDR protein has a relatively short C-terminal tail following the catalytic domain (8 amino acids in DDR versus 13 in trka). The C-terminal tail of DDR does not contain tyrosine residues, but the tyrosine residues conserved within the catalytic domains of trkA and the insulin receptor are also conserved in DDR. This includes DDR tyrosines 793, 797, and 798, which by analogy with the insulin receptor are autophosphorylation sites. The exceptionally long cytoplasmic juxtamembrane region contains an Asn-Pro-Ala-Tyr (SEQ ID NO:5) sequence characteristic of the tight turn recognition motif for internalization in coated pits (Chen, W. J., Goldstein, J. L. & Brown, M. S. (1990) *J. Biol. Chem.* 265,3116–3123 and Bansal, A. & Gierasch, L. M. (1991) *Cell* 67, 1195–201, which are incorporated herein by reference).

Figure 3:
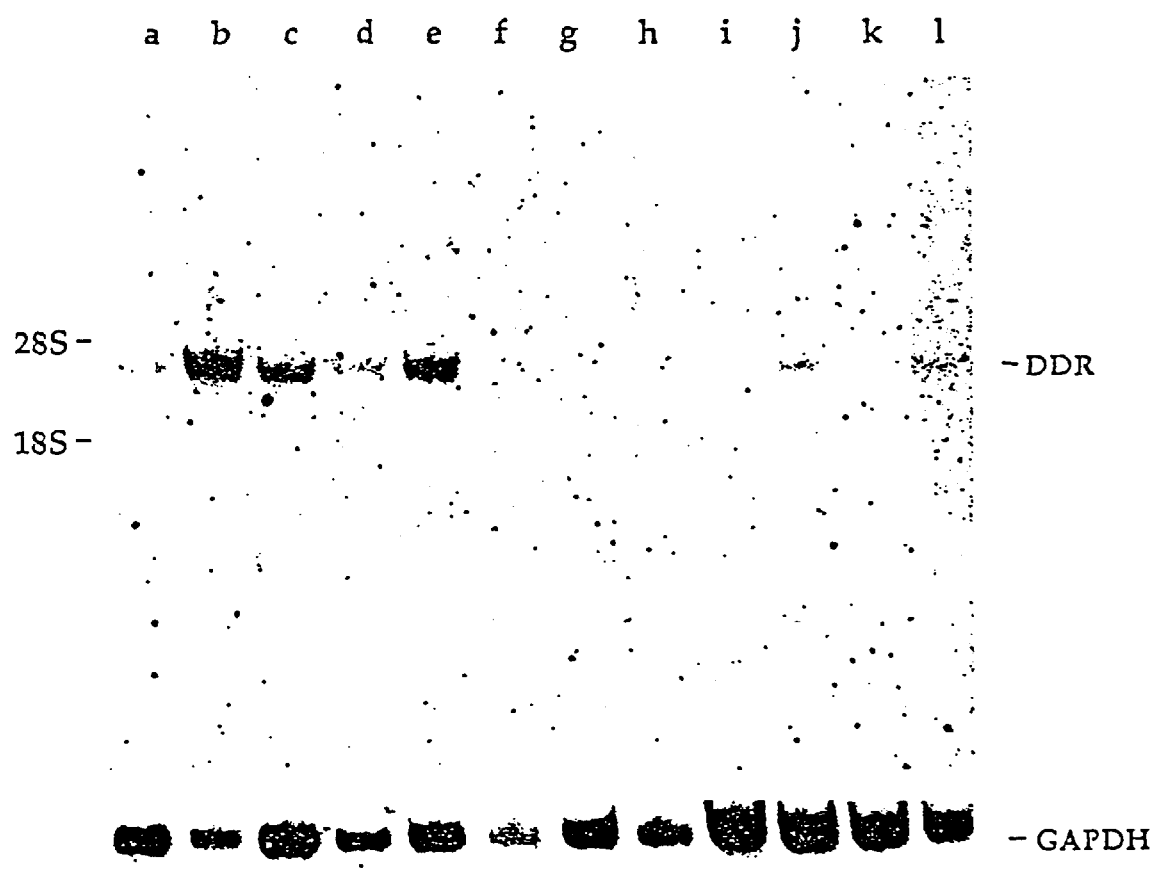
FIG. 3 shows a Northern analysis of DDR transcripts in human cell line total RNAs. Total RNAs (20 micrograms) from human cell lines a BeWo, b T-47D, c MCF-7, d PANC-1, e A431, f U937, g Daudi, h HL-60, i Jurkat, j C32, k HepG2, I HeLa were fractionated on formaldehyde agarose gels, transferred to a nitrocellulose filter and hybridized with a 0.5 kilobase $^{32}$P-labeled PCR product encompassing nucleotides 213 to 772 of the DDR cDNA in 50% formamide at 42° C. After washing and exposure to film for 3 days, the filter was subsequently probed with a $^{32}$P-labeled mouse GAPDH (glyceraldehyde 3-phosphate dehydrogenase) cDNA to confirm that a similar amount of RNA was loaded in each lane. The migrations of the DDR and GAPDH transcripts as well as the ribosomal RNAs are indicated.

Northern analysis of multiple human cell lines demonstrated that a 4.0 kilobase DDR transcript is relatively abundant in the human breast carcinoma cell lines T-47D, BT-20 and MCF-7 and also relatively high in the A431 epidermoid carcinoma cell line (FIG. 3). Transcripts hybridizing with the DDR cDNA were found in polyA+RNAs from multiple mouse tissues, but in widely varying amounts (FIG. 4). Kidney, spleen and placenta had the highest levels of the 4.0 kilobase transcript relative to the levels of GAPDH (glyceraldehyde 3-phosphate dehydrogenase) mRNA in each preparation.

Figure 5:
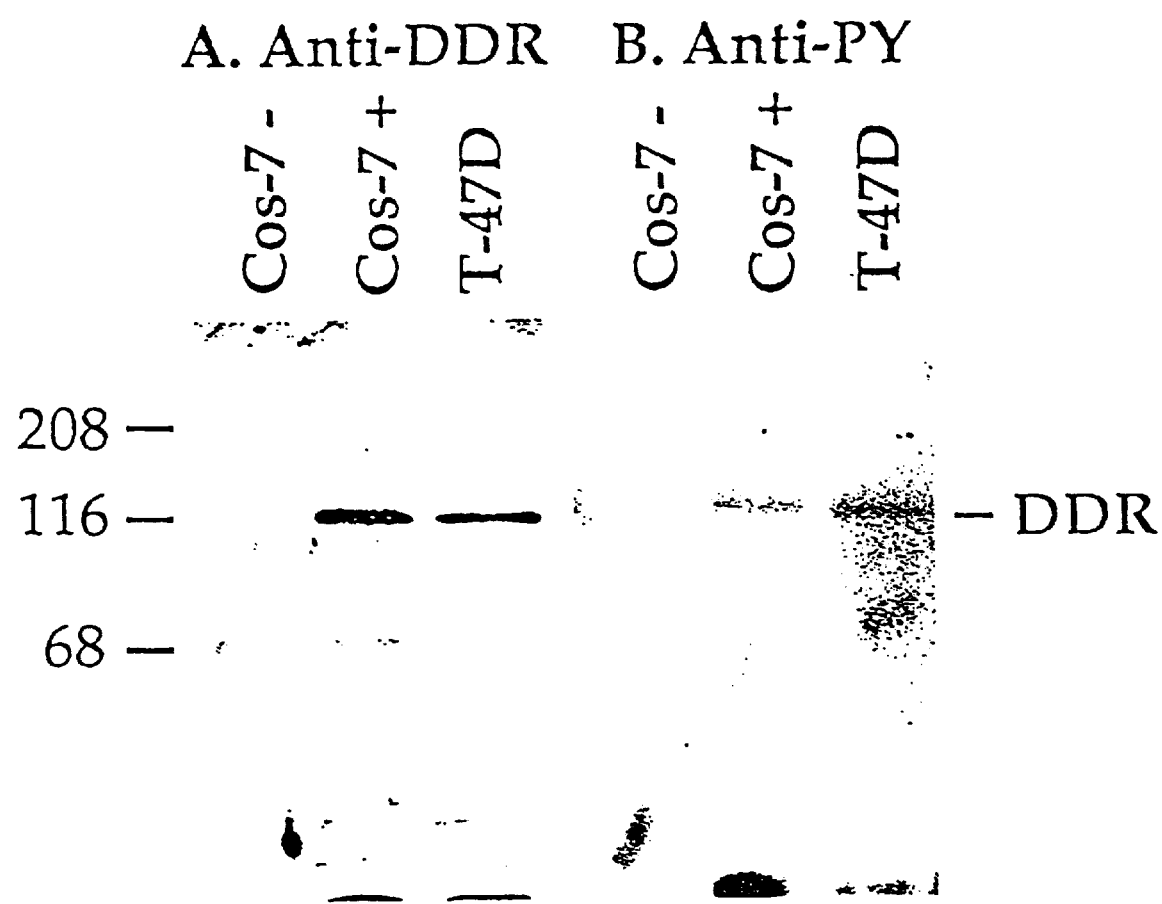
FIG. 5 shows DDR polypeptide and tyrosine phosphorylation in transfected COS-7 cells and T47D breast carcinoma cells. Wheat germ agglutinin binding extracts of untransfected COS-7 cells, COS-7 cells transfected with the DDR cDNA and T47D cells were fractionated on 7.5% NaDodSO$_4$-PAGE for immunoblot analysis with anti-DDR antiserum e.1 as described below in the Examples section. The filter was stripped of antibodies as described below in the Examples section, incubated with detection reagents to ensure stripping and then tyrosine phosphoproteins were detected with antibody PY20. In other experiments two tyrosine phosphoprotein bands were observed: one the size of DDR and the other at approximately 180 kDa. The mobilities of prestained protein markers are shown at the right.

To characterize the DDR polypeptide, we transfected COS-7 cells with the DDR cDNA in a mammalian expression vector. Wheat germ agglutinin-binding extracts of transfected cells contained a 120 kDa DDR protein that was reactive with antisera developed against a lacZ fusion protein containing a portion of the extracellular domain of the DDR- encoded polypeptide (FIG. 5, anti-DDR). The DDR protein was also specifically reactive with an antiphosphotyrosine antibody presumably due to autophosphorylation (FIG. 5, anti-PY). The DDR protein was also detected in T47D and BT-20 breast carcinoma cell lines, but was not detected in a variety of other human cell lines (FIG. 5 and data not shown). The major tyrosine phosphoprotein present in wheat germ agglutinin-binding extracts of T-47D cells had an identical electrophoretic mobility to the DDR protein (FIG. 5).

We have characterized a novel putative receptor tyrosine kinase, DDR, that is abundant in breast carcinoma cell lines. DDR has at least two unusual features, the discoidin I-type domain and the extensive proline/glycine-rich regions, not present in other receptor tyrosine kinases. These features suggest that DDR may have an unusual mechanism of transmembrane signaling or an unusual ligand.

The presence of a discoidin I-type domain in the ectodomain of a receptor tyrosine kinase is provocative. Discoidin I is a *Dictyostelium discoideum* lectin that participates in cell aggregation (Springer, W. R., Cooper, D. N. W. & Barondes, S. H. (1984) *Cell* 39, 557–564, which is incorporated herein by reference). Discoidin I-type domains (Poole, S., Firtel, R. A., Lamar, E. & Rowenkamp, W. (1981) *J. Mol. Biol.* 153, 273–289, which is incorporated herein by reference) are present as tandem repeats at the C-terminus of the light chains of factor V (Kane, W. H. & Davie, E. W. (1986) *Proc. Natl. Acad. Sci. U.S.A.* 83, 6800–6804, which is incorporated herein by reference) factor Vil (Toole, J. J., Knopf, J. L., Wozney, J. M., Sultzman, L. A., Buecker, J. L., Pittman, D. D., Kaufman, R. J., Brown, E., Shoemaker, C., Orr, E. C., Amphlett, G. W., Foster, W. B., Coe, M. L., Knutson, G. J., Fass, D. N. & Hewick, R. M. (1984) Nature 312, 342–347 and Vehar, G. A., Keyt, B., Eaton, D., Rodriguez, H., O'Brien, D. P., Rotblat, F., Oppermann, H., Keck, R., Wood, W. I., Harkins, R. N., Tuddenham, E. G. D., Lawn, R. M. & Capon, D. J. (1984) *Nature* 312, 337–342, which are incorporated herein by reference) and two milk fat globule membrane proteins, MFG.E8 (Stubbs, J. D., Lekutis, C., Singer, K. L., Bui, A., Yuzuki, D., Srinivasan, U. & Parry, G. (1990) *Proc. Natl. Acad. Sci. USA* 87, 8417–8421, which is incorporated herein by reference) and BA46 (Larocca, D., Peterson, J. A., Urrea, R., Kuniyoshi, J., Bistrain, A. M. & Ceriani, R. L. (1991) *Cancer Research* 51, 4994–4998, which is incorporated herein by reference). The role of the discoidin I-type domains in these proteins is not completely understood, but there is evidence suggesting that the light chains of factor V and VIII interact with specific platelet membrane proteins (Tracey, P. B., Peterson, J. M., Nesheim, M. E., McDuffie, F. C. & Mann, K. G. (1979)*J. Biol. Chem.* 254,10354–10361, Tracey, P. B., Nesheim, M. E. & Mann, K. G. (1980) *J. Biol. Chem.* 255, 662–669, and Nesheim, M., Pittman, D. D., Wang, J. H., Slonosky, D., Giles, A. R. & Kaufman, R. J. (1988) *J. Biol. Chem.* 263, 16467–16470, which are incorporated herein by reference), and MFG.E8 and BA46 are stably associated with mammary epithelial membranes (Stubbs, J. D., Lekutis, C., Singer, K. L., Bui, A., Yuzuki, D., Srinivasan, U. & Parry, G. (1990) *Proc. Natl. Acad. Sci. USA* 87, 8417–8421 and Larocca, D., Peterson, J. A., Urrea, R., Kuniyoshi, J., Bistrain, A. M. & Ceriani, R. L. (1991) *Cancer Research* 51, 4994–4998, which are incorporated herein by reference). Recently, tandem discoidin I-type domains have also been found in the extracellular region of a cell surface transmembrane protein, A5 (Takagi, S., Hirata, T., Agata, K., Mochii, M., Eguchi, G. & Fujisawa, H. (1991) Neuron 7, 295–307, which is incorporated herein by reference), which has a small (44 amino acids) cytoplasmic region. Since this protein has a highly specific localization at the termination site of the optic nerve and is expressed contemporaneously with optic nerve innervation, it has been proposed that A5 is a targeting molecule for retinal axons (Takagi, S., Tsuji, T., Amagai, T. & Fujisawa, H. (1987) *Dev. Biol.* 122, 90–100, which is incorporated herein by reference). A highly conserved consensus sequence can be derived from an alignment of the discoidin I-type domains in these proteins (Poole, S., Firtel, R. A., Lamar, E. & Rowenkamp, W. (1981) *J. Mol. Biol.* 153, 273–289, Larocca, D., Peterson, J. A., Urrea, R., Kuniyoshi, J., Bistrain, A. M. & Ceriani, R. L. (1991) *Cancer Research* 51, 4994–4998, Stubbs, J. D., Lekutis, C., Singer, K. L., Bui, A., Yuzuki, D., Srinivasan, U. & Parry, G. (1990) *Proc. Natl. Acad. Sci.* 87, 8417–8421, Kane, W. H. & Davie, E. W. (1986) *Proc. Natl. Acad. Sci. U.S.A.* 83, 6800–6804, Vehar, G. A., Keyt, B., Eaton, D., Rodriguez, H., O'Brien, D. P., Rotblat, F., Oppermann, H., Keck, R., Wood, W. I., Harkins, R. N., Tuddenham, E. G. D., Lawn, R. M. & Capon, D. J. (1984) *Nature* 312, 337–342, and Takagi, S., Hirata, T., Agata, K., Mochii, M., Eguchi, G. & Fujisawa, H. (1991) *Neuron* 7, 295–307). The mammalian members of the group also have similarities outside the region of similarity with discoidin I. The DDR discoidin I-type domain adheres closely to a consensus sequence defined by the other discoidin domain containing proteins. Analogy with the other discoidin I-type domain containing proteins suggests that the DDR ligand may be a cell surface molecule. Since DDR is relatively abundant in breast carcinoma cells, it is particularly intriguing that mammary epithelial membranes appear to express a component that binds BA46 (Larocca, D., Peterson, J. A., Urrea, R., Kuniyoshi, J., Bistrain, A. M. & Ceriani, R. L. (1991) *Cancer Research* 51, 4994–4998, which is incorporated herein by reference). Characterization of the DDR ligand could reveal a set of interactions involved in multiple biological regulatory systems.

The two juxtamembrane regions of DDR suggest a unique signaling mechanism for DDR. Out of 180 residues in the regions indicated in FIGS. 1 and 2, 46 are proline and 19 are glycine (36% is P+G). The region between the discoidin I-type domain and this extremely proline/glycine-rich region is also glycine-rich; therefore the 250 amino acid connecting region between the discoidin I-type domain and the tyrosine kinase domain, excluding the transmembrane and stop-transfer regions, is 25% proline/glycine. The extensive hydrophilic proline/glycine-rich region of DDR does not contain collagen-like repeating motifs, nor does it contain sequence patterns characteristic of the family of salivary proline-rich proteins. The 176 residue cytoplasmic juxtamembrane region is the longest described for any receptor tyrosine kinase (over three times longer than the average juxtamembrane span in the insulin receptor family of tyrosine kinases). Proline/glycine-rich regions like the one found in DDR are potentially flexible, but the physical properties of this region remain to be experimentally determined. A proline/glycine-rich region of the type found in DDR has not previously been observed in an integral membrane protein. However, regions of similar composition and length are found within the adaptins, which tether transmembrane proteins (e.g. receptors) to clathrin-coated pits and vesicles (Robinson, M. S. (1989) *J. Cell Biol.* 108, 833–842, Ponnambalam, S. Robinson, M. S., Jackson, A. P., Peiper, L. & Parham, P. (1990) *J. Biol. Chem.* 265, 4814–4820, Kirchhausen, T., Nathanson, K. L., Matsui, W., Vaisberg, A., Chow, E. P., Burne, C., Keen, J. H. & Davis, A. E. (1989) *Proc. Natl. Acad. Sci. USA* 86, 2612–2616, Robinson, M. S. (1990) *J. Cell Biol.* 111, 2319–2326, Virshup, D. M. & Bennett, V. (1988) *J. Cell Biol.* 106, 39–50, and Heuser, J. E. & Keen, J. (1988) *J. Cell Biol.* 107, 877–886, which are incorporated herein by reference). The corresponding regions of a (Robinson, M. S. (1989) *J. Cell Biol.* 108, 833–842), b (Ponnambalam, S. Robinson, M. S., Jackson, A. P., Peiper, L. & Parham, P. (1990) *J. Biol. Chem.* 265, 4814–4820 and Kirchhausen, T., Nathanson, K. L., Matsui, W., Vaisberg, A., Chow, E. P., Bume, C., Keen, J. H. & Davis, A. E. (1989) *Proc. Natl. Acad. Sci. USA* 86, 2612–2616, which are incorporated by reference) and d-adaptins (Robinson, M. S. (1990) *J. Cell Biol.* 111, 2319–2326, which is incorporated herein by reference) are 34%, 26% and 27% proline+glycine over 96, 152, and 125 residues, respectively. Electron microscopic examination of adaptins demonstrates two globular domains connected by an extended hinge (Virshup, D. M. & Bennett, V. (1988) *J. Cell Biol.* 106, 39–50 and Heuser, J. E. & Keen, J. (1988) *J. Cell Biol.* 107, 877–886, which are incorporated herein by reference). The DDR proline/glycine-rich region does not contain sequence patterns similar to the adaptin hinge regions. The a and b adaptins, however, also do not have sequence motifs conserved between their respective hinge regions; it appears that overall amino acid composition determines hinge formation rather than a specific sequence pattern (Takagi, S., Tsuji, T., Amagai, T. & Fujisawa, H. (1987) *Dev. Biol.* 122, 90–100, which is incorporated herein by reference). The adaptin hinges appear to be required to bridge the physical gap between clathrin and plasma membrane proteins in coated pits or vesicles (Ponnambalam, S. Robinson, M. S., Jackson, A. P., Peiper, L. & Parham, P. (1990) *J. Biol. Chem.* 265, 4814–4820, Kirchhausen, T., Nathanson, K. L., Matsui, W., Vaisberg, A., Chow, E. P., Bume, C., Keen, J. H. & Davis, A. E. (1989) *Proc. Natl. Acad. Sci. USA* 86, 2612–2616, Robinson, M. S. (1990) *J. Cell Biol.* 111, 2319–2326, Virshup, D. M. & Bennett, V. (1988) *J. Cell Biol.* 106, 39–50, and Heuser, J. E. & Keen, J. (1988) *J. Cell Biol.* 107, 877–886, which are incorporated herein by reference). The proline/glycine-rich regions of the DDR may serve an analogous tethering function and allow a unique geometry in interaction with the ligand or allow access of the tyrosine kinase domain to a unique set of substrates.

Elucidation of the physical characteristics and ligand binding properties of DDR should provide insight into a unique transmembrane signaling process.

Several important uses of the subject invention are disclosed. First, the DDR cDNA or antibody reagents generated from the sequence may be useful for diagnostic or prognostic analysis of tumors of the breast and lung. Antibodies to the extracellular domain may be useful for screening blood or other tissue samples.

Second, the recombinant DDR extracellular domain should allow purification and characterization of the ligand. Identification of the ligand is important for designing therapeutic agents which might act via the DDR to influence the behavior of breast and lung tumors.

Third, the recombinant DDR extracellular domain is a potential immunogen for active immunotherapy of breast and lung cancer.

Fourth, the recombinant DDR extracellular domain may block the normal function of the receptor in vivo by occupying the ligand. This could inhibit the growth of tumors that require growth signals from activated DDR.

Clarifying and expanding on the above possible uses, the primary sequence of the DDR cDNA predicts a transmembrane protein that contains an N-terminal discoidin I-like domain, a membrane spanning region and a C-terminal tyrosine kinase domain. The presence of a tyrosine kinase domain suggests that the DDR protein is involved in transmembrane control of the growth status of the cell. The presence of an extracellular discoidin I-type domain, which is unique to DDR among receptor tyrosine kinases, suggests that DDR interacts with a ligand found on cell surfaces or within the extracellular matrix. Since discoidin I is a lectin, it is possible that the DDR ligand will have a carbohydrate component.

The DDR cDNA has also provided the means to define the nature of the ligand. Recombinant forms of the subject DDR cDNA have been used to obtain protein reagents corresponding to fragments or rearrangements of the predicted protein. The N-terminal portion of the DDR cDNA has been truncated to encode an extracellular domain fragment corresponding to amino acids 1–387 of the predicted protein sequence, which includes the signal peptide, the DLD and a portion of the juxtamembrane region, to which specific antiserum has been obtained. Identification of the ligand involves development of binding assays to determine the localization of the ligand within tissues and to define the molecular determinants of DDR ligand-receptor interactions. This type of binding assay will permit determining the exact carbohydrate binding determinants.

It is clear that DDR itself is present in several different types of human tumor cell lines that originated in specific types of epithelia. If the DDR ligand is present within such tumors, then blocking its interaction with DDR may influence the survival of the tumor. Soluble DDR derived reagents may be able to directly block the DDR-ligand interactions and could be used to screen compounds for the ability to block the receptor-ligand interaction. For example, if there is a carbohydrate component of interaction of the ligand with DDR, specific carbohydrates may be able to block growth stimuli normally or abnormally mediated by the DDR polypeptide.

A portion of the DDR cDNA has been used to aid in generating a polyclonal antibody specific for the extracellular domain of the DDR polypeptide. This and other antibodies which are generated as a result of the DDR cDNA sequences could have prognostic value in the analysis of specific tumors of epithelial origin. Since the extracellular domain of receptors are often shed from the cell surface and can be subsequently found in serum samples, antibodies such as the one generated here could be useful for screening blood samples for the presence of the DDR extracellular domain. If the DDR molecule is found to have prognostic value for specific tumors, the ability assay for its presence in blood samples could have value for non-invasive screening and diagnosis.

The DNA sequence disclosed herein has been assigned Genbank accession number L11315.

EXAMPLES

Example 1 cDNA Cloning and Characterization

A full term human placental lgt10 cDNA library was screened with a $^{32}$P-labeled antisense oligonucleotide of the sequence 5'-GTT(G/C)CG(A/G)GC(A/G)GCCAG(A/G)TC-(G/C)CG(A/G)TG-3' (SEQ ID NO: 3), corresponding to the His-Arg-Asp-Leu-Ala-Ala-Arg-Asn (SEQ ID NO:6) amino acid sequence found in many tyrosine kinases, by methods described previously (Fischman, K., Edman, J. C., Shacklefor, G. M., Turner, J. A., Rutter, W. J. & Nir, U. (1990) *Mol. Cell. Biol.* 10, 146–153, which is incorporated herein by reference). Positive clones were grouped by cross-hybridization and plaque isolated for subcloning in M13 derivatives or plasmids for sequencing with Sequenase (USB) and an ABI 370A automated sequencer. Three individual clones from a class of 19 had identical nucleotide sequence tags and overlapping restriction maps. Both strands of the DDR cDNA in one of these were sequenced in their entirety. This sequence has one long open reading frame (nucleotides 88 to 2883) which is followed by a polyadenylation signal (at nucleotide 3721) and a polyadenine tract (SEQ ID NO: 1). The first in-frame methionine (at nucleotide 142) has a Kozak consensus sequence (Kozak, M. (1987) *Nucleic Acids Res.* 15, 8125–8148, which is incorporated herein by reference) followed by a predicted signal peptide that initiates a precursor protein of 914 amino acids (SEQ ID NO: 2). A second hydrophobic region (residues 419–437) conforms to expectations for a membrane-spanning domain.

Example 2

Northern Analysis

RNAs were prepared using RNAzol (CinnaBiotecx) reagent and protocols. Formaldehyde-agarose fractionated RNAs were transferred to nitrocellulose and hybridized as described previously (Harlow, E. & Lane, D. (1988) *Anti-* bodies: A Laboratory Manual, Cold Spring Harbor Laboratory, Cold Spring Harbor, N.Y., which is incorporated herein by reference) with $^{32}$P-labeled DDR cDNA fragments described in the figure descriptions. Filters were subsequently probed with a $^{32}$P-labeled GAPDH (glyceraldehyde 3-phosphate dehydrogenase) cDNA.

Example 3

Production of Anti-DDR Antisera e.1

A Sal I-Eco RI fragment of the DDR cDNA was subcloned to pUR290 to allow production of a b-galactosidase fusion (Harlow, E. & Lane, D. (1988) *Antibodies: A Laboratory Manual*, Cold Spring Harbor Laboratory, Cold Spring Harbor, N.Y., which is incorporated herein by reference) of DDR residues 223 to 346 within the extracellular region of the protein. The fusion protein was purified by NaDodSO$_4$-PAGE for rabbit immunization (Harlow, E. & Lane, D. (1988) *Antibodies: A Laboratory Manual*, Cold Spring Harbor Laboratory, Cold Spring Harbor, N.Y., which is incorporated herein by reference).

Example 4

Transient Expression of Human DDR in COS-7 Cells

The DDR cDNA was subcloned into the Eco RI site of the mammalian expression vector pECE (Ellis, L., Clauser, E., Morgan, D. O., Edery, M., Roth, R. A. & Rutter, W. J. (1986) *Cell* 45, 721–732, which is incorporated herein by reference). This plasmid, pSV33, was used to transfect COS-7 cells by the DEAE-dextran method (Kaufman, R. J. (1990) *Meth. Enz.* 185, 487–511, which is incorporated herein by reference). After 48 hours the cells were solubilized in NaDodSO$_4$-PAGE sample buffer for immunoblotting.

Example 5

Immunoblotting

Cells on 10 cm plates were solubilized in 1.0 ml of RIPA buffer containing 1% Triton X-100, 20 mM Tris-HCl pH 7.5, 50 mM sodium chloride, 1 mM sodium orthovanadate, 1 mM PMSF, 50 mM sodium fluoride, 5 mM EDTA and 20 mM sodium pyrophosphate at 4° C. Samples were centrifuged for 15 minutes at 10,000×g at 4° C. and the supernatants were rocked with 50 ml of wheat germ agglutinin agarose (Vector) for 1.5 h. The beads were washed three times with RIPA buffer and boiled in 100 ml of NaDodSO$_4$-PAGE sample buffer. Samples were fractionated on 7.5% NaDodSO$_4$-PAGE, transferred to Immobilon-P (Millipore) and incubated with a 1:500 dilution of rabbit antiserum e.1 (see above) in 5% nonfat dry milk in phosphate buffered saline and subsequently incubated with horseradish peroxidase (HRP)-coupled sheep anti-rabbit IgG for detection with ECL (Amersham) reagents. The filters were stripped of antibodies with 100 mM 2-mercaptoethanol, 2% NaDodSO$_4$, 62.5 mM Tris-HCl pH 6.7 for 30 minutes at 50° C. The filters were washed and incubated with HRP-sheep anti-rabbit IgG and ECL reagents as before to ensure that all antibodies were removed. The filters were then incubated with a 1:1000 dilution of the monoclonal antiphosphotyrosine antibody PY20 (ICN), and subsequently with $^{125}$1-protein A (ICN) (Harlow, E. & Lane, D. (1988) *Antibodies: A Laboratory Manual*, Cold Spring Harbor Laboratory, Cold Spring Harbor, N.Y., which is incorporated herein by reference) prior to autoradiography.

The invention has now been explained with reference to specific embodiments. Other embodiments will be suggested to those of ordinary skill in the appropriate art upon review of the present specification.

Although the foregoing invention has been described in some detail by way of illustration and example for purposes of clarity of understanding, it will be obvious that certain changes and modifications may be practiced within the scope of the appended claims.

What is claimed is:

1. An isolated and purified polypeptide which has a sequence of amino acids shown in SEQ ID NO:2 and has a first domain with discoidin-type ligand binding characteristics, and a second domain with tyrosine kinase activity.

2. An isolated and purified polypeptide which has a sequence of amino acids shown in SEQ ID NO:2 and has a first domain with carbohydrate binding activity, and a second domain with tyrosine kinase activity.

* * * * *